(12) United States Patent
Adam et al.

(10) Patent No.: US 11,701,002 B2
(45) Date of Patent: Jul. 18, 2023

(54) DISTRIBUTED NEUROMORPHIC COMPUTING FOR HIGH DEFINITION BIOELECTRIC DIAGNOSTICS AND THERAPY

(71) Applicant: The George Washington University, Washington, DC (US)

(72) Inventors: Gina C. Adam, Washington, DC (US); Igor R. Efimov, Washington, DC (US)

(73) Assignee: The George Washington University, Washington, DC (US)

( * ) Notice: Subject to any disclaimer, the term of this patent is extended or adjusted under 35 U.S.C. 154(b) by 612 days.

(21) Appl. No.: 16/780,523

(22) Filed: Feb. 3, 2020

(65) Prior Publication Data

US 2020/0245870 A1 Aug. 6, 2020

Related U.S. Application Data

(60) Provisional application No. 62/800,175, filed on Feb. 1, 2019.

(51) Int. Cl.
| | |
|---|---|
| *A61B 5/00* | (2006.01) |
| *A61B 5/0205* | (2006.01) |
| *A61N 1/36* | (2006.01) |
| *A61N 1/05* | (2006.01) |
| *G06N 3/063* | (2023.01) |
| *A61B 5/24* | (2021.01) |

(52) U.S. Cl.
CPC .............. *A61B 5/0031* (2013.01); *A61B 5/24* (2021.01); *A61N 1/05* (2013.01); *A61N 1/36125* (2013.01); *A61N 1/36135* (2013.01); *G06N 3/063* (2013.01); *A61B 2562/066* (2013.01)

(58) Field of Classification Search
CPC .............. A61M 60/122; A61M 60/148; A61M 60/268; A61M 60/40
See application file for complete search history.

(56) References Cited

U.S. PATENT DOCUMENTS

| | | | | |
|---|---|---|---|---|
| 2016/0287177 | A1* | 10/2016 | Huppert | ................. A61B 5/486 |
| 2016/0346449 | A1* | 12/2016 | Roche | ................... F15B 15/103 |

OTHER PUBLICATIONS

L. Xu et al., "3D Multifunctional Integumentary Membranes for Spatiotemporal Cardiac Measurements and Stimulation Across the Entire Epicardium," Nature Communications, vol. 5, pp. 1-10, 2014.
S. R. Gutbrod, et al., "Patient-Specific Flexible and Stretchable Devices for Cardiac Diagnostics and Therapy," Progress in Biophysics and Molecular Biology, vol. 115, No. 2-3, pp. 2-16, Aug. 2014.

(Continued)

*Primary Examiner* — Jon Eric C Morales
(74) *Attorney, Agent, or Firm* — Blank Rome LLP (57) ABSTRACT

A medical apparatus for an organ has a substrate that conforms to a shape of the organ, and a plurality of processing units connected to the substrate and distributed throughout the substrate. Each of the processing units has a sensor, processing device and actuator. The sensor senses a condition of the organ and provides a sensed signal. The processing device receives the sensed signal from said sensor, analyzes the sensed signal and provides a control signal. The actuator applies an output pulse to the organ in response to the control signal from the processing device.

26 Claims, 6 Drawing Sheets

(56) References Cited

OTHER PUBLICATIONS

A. H. Janardhan, et al., "A Novel Low-Energy Electrotherapy That Terminates Ventricular Tachycardia With Lower Energy Than a Biphasic Shock When Antitachycardia Pacing Fails," Journal of the American College of Cardiology, vol. 60, No. 23, pp. 2393-2398, Dec. 2012.

G. C. Adam, et al., "3-D Memristor Crossbars for Analog and Neuromorphic Computing Applications," IEEE Transactions on Electron Devices, vol. 64, No. 1, pp. 312-318, Jan. 2017.

S. P. Adhikari, et al., "Building Cellular Neural Network Templates with a Hardware Friendly Learning Algorithm," Neurocomputing, vol. 312, pp. 1-17, 2018.

M. Prezioso, et al., "Training and Operation of an Integrated Neuromorphic Network Based on Metal-Oxide Memristors" Nature, vol. 521, No. 7750, pp. 61-64, May 2015.

W. Zhang, et al., "CMOL-Based Cellular Neural Networks and Parallel Processor for Future Image Processing," in Proceedings of the 8th IEEE Conference on Nanotechnology, pp. 737-740, 2008.

\* cited by examiner

FIG. 6

DISTRIBUTED NEUROMORPHIC COMPUTING FOR HIGH DEFINITION BIOELECTRIC DIAGNOSTICS AND THERAPY

RELATED APPLICATIONS

This application claims the benefit of U.S. Provisional Application No. 62/800,175, filed Feb. 1, 2019, the entire contents of which are incorporated herein by reference.

BACKGROUND OF THE INVENTION

Field of the Invention

The present invention relates to a system for bioelectric diagnostics and therapy. More particularly, the present invention relates to a system for bioelectric diagnostics and therapy using distributed neuromorphic computing.

Background of the Related Art

Bioelectric signals govern the functionality of a number of vital human organs, like the brain, heart, muscles, gut, etc. Since bioelectric anomalies can hint to severe health conditions, acting on the basis of this data is key for smart diagnostics and real time therapy. The state-of-the-art approach uses bio-compatible sensor and actuator arrays integrated in an organ conformal substrate, which enables local data gathering, processing, and actuation. However, no existing system has embedded computing capability for local interpretation of the data and millisecond decision-making, as required for real-time life-saving therapy.

Ventricular tachyarrhythmias are responsible for 300,000 sudden cardiac deaths a year in the US. Ventricular fibrillation is the most severe. Very rapid erratic heartbeats prevent pumping of blood and causes death within minutes. On-going scientific and clinical research is needed to understand the spatiotemporal complexity of wave propagation in arrhythmias and find treatment. Advanced engineering solutions are required for this, with innovative computing technologies being crucial due to difficult real-time data processing constraints.

Organ conformal electronics platforms with non-contact sensors can be used for in vivo experiments for mapping of the electrical activity across the entire ventricle [1] but have limited spatial and temporal resolution. Efforts to increase the density of sensors and embed also actuators for therapy are underway [2], promising a personalized electrotherapy solution to terminate life threatening tachycardias with >1-2 orders of magnitude less energy than a typical shock [3].

SUMMARY OF THE INVENTION

A medical apparatus for an electrically active organ has a mechanically flexible and stretchable substrate that conforms to a shape of the organ, and a plurality of processing units connected to the substrate and distributed throughout the substrate. Each of the processing units has a sensor, processing structure and actuator. The sensor senses a physiological parameter of the organ and provides an electrical signal representing this parameter. The processing device receives the electrical signal from said sensor, analyzes the electrical signals from this and other sensors, and provides a control signal. The actuator applies an output stimulus to the organ in response to the control signal from the processing device.

BRIEF DESCRIPTION OF THE FIGURES

FIGS. 1(a)-1(c) show a closed-loop organ conformal platform combining sensing, computing and actuation, where FIG. 1(a) describes the functionality of the distributed network of smart processing units.

FIGS. 2(a), (b) are schematics of the distributed computing approach using programmable templates.

FIGS. 3(a), 3(b) show memristor technology which can be used to store the programmable template matrices in a small and compact manner.

DETAILED DESCRIPTION OF THE INVENTION

In describing the illustrative, non-limiting embodiments of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose. Several embodiments of the invention are described for illustrative purposes, it being understood that the invention may be embodied in other forms not specifically shown in the drawings.

Figure 1A:
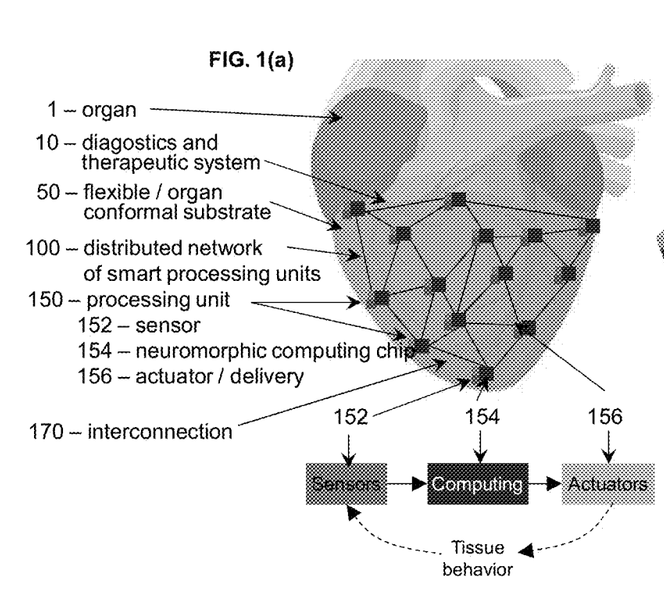

This invention provides a distributed computing solution that can be reliably and monolithically integrated with existing and future biosensor and actuators platforms on flexible/stretchable or organ conformal substrates (FIG. 1). Referring to FIG. 1(a), an implantable diagnostics and therapeutic system (10) made of a flexible and/or stretchable or organ conformal substrate (50) with integrated electronics (100) can be positioned on an organ (1), for example covering the entire ventricle, during surgery on animal or human subjects for research or therapeutic purposes. The substrate (50) can also be, for example, a patch or sleeve. This system (10) can be powered up by an energy storage source or an energy harvesting system (not shown for clarity). A distributed electronic network (100) includes a plurality of smart processing units (150). Each processing unit (150) includes a sensor (152), a neuromorphic computing chip (154) and an actuator/delivery device (156).

Figure 1B:
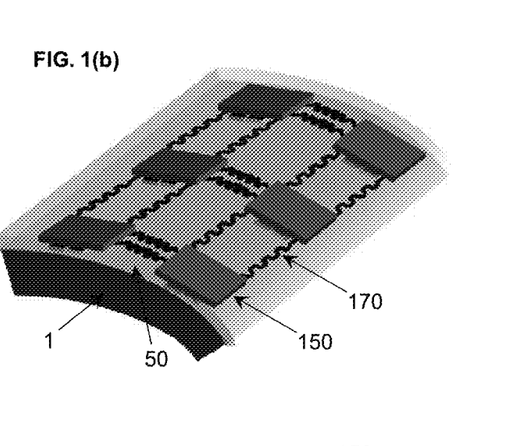
FIG. 1(b) shows a three dimensional detail on the interconnectivity of the processing units.
Figure 1C:
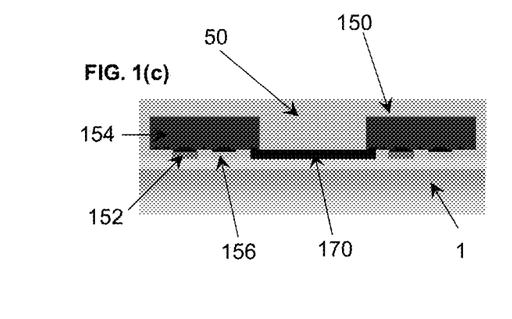
FIG. 1(c) shows a cross-section that highlights the sensor and actuator in proximity of the tissue and the computing chip above them in flipped position to ensure contact.

The processing units (150) are linked by stretchable interconnections (170) as shown in FIG. 1(b). The interconnections (170) need to compensate for the stretching and contracting of the flexible substrate during the muscle contraction/relaxation of the heart beat. To facilitate this, they can be fabricated in a serpentine configuration e.g., the back and forth S-shape (shown in FIG. 1b) or can be made of conductive stretchable polymers (not shown). FIG. 1(c) shows an example of a potential implementation where the sensor (152) and the actuator/delivery device (156) are in close proximity with the organ tissue (1). They connect to the neuromorphic computing chip (154) which has its circuit and connection pads facing down to interface with the sensor and the actuator. The neuromorphic computing chip also has connection pads to interface with other neuromorphic computing chips via stretchable interconnections (170).

The sensor (152) and actuator/delivery device (156) are in physical contact with the computing chip (154). The computing chip (154) is placed face down, facing the sensor (152) and the actuator (156) to allow for direct electrical connectivity and transfer of data between the chip (154) and the sensor (152), and between the chip (154) and the actuator (156). Various fabrication routes can be employed to achieve this goal. For example, the sensor (152), the actuator (156) and the interconnections (170) can be first fabricated on the flexible/stretchable or organ conformal substrate (50). The fabrication process of the sensors and interconnections on an organ conformal substrate can be in accordance with any suitable process, such as found at reference [1] below. Then, conductive polymers can be added on the sensor (152), the actuator (156) and the interconnections (170) at the points of contact with the chip (154) to facilitate the mechanical bonding and the electrical connectivity. The computing chip (154) can be then placed face down and aligned to match the desired points of contact to the sensor (152), the actuator (156) and the interconnections wires (170). That is, the sensor (152), actuator (156) and interconnections (170) are directly mounted/connected to (by bonding) the chip (154). The entire structure can be then be encapsulated in a film of insulating stretchable polymer to ensure the mechanical robustness of the structure and isolate it from body for implantation. For example, a silicone elastomer, such as Ecoflex with low modulus and high biocompatibility can be poured and cured on top of the structure to achieve this purpose.

To increase the resolution (i.e., the amount of detail that the distributed network (100) can sense and deliver properly timed therapy to the specific affected area of the tissue), the processing units (150) should be as small and as densely packed as possible. The sensors, processing chips and actuators can have any suitable size based on the desired application and functionality, such as those shown in reference [2]. The sensors (152) and actuators (156) can be implemented with stretchable materials. The neuromorphic computing chip (154) can be implemented with traditional CMOS technology, typical of ASIC developments. This is not a flexible/stretchable component, so it is important to miniaturize its size as much as possible.

In a non-distributed implementation, one computing chip processing data in real-time from thousands of sensors could have dimensions of cm. By distributing the computation to a network of computing chips, each chip can be process data from only one sensor and can be made very small. For example, 50 μm to 500 μm lateral dimensions would provide enough circuit area to implement desired functionality and be non-intrusive to the moving tissue of the beating heart. The relative size of the computing chip to the sensor and actuator is dependent on the manufacturing technology and desired functionality. For example, the size of the sensors can be <500 μm [1]. If the computing chip is added in a stacked configuration on top the sensor and the actuator as shown in FIG. 1, the chip (154) area can be similar in size to the combined area of the sensor (152) and the actuator (156), for optimal density and computational power, as long as the chip size is non-intrusive and there is no electrical crosstalk between the devices. The devices can be ~50-500 μm apart, but the exact density of sensors needed to properly map the electrical activity with optimal spatial resolution is likely to be comparable or exceed the space constant of cardiac tissue (~500 μm-1 mm). This invention will also help with optimization research in this area.

The computing chip (154) can a custom designed Application Specific Integrated Component (ASIC). A neuromorphic computing chip in particular could offer several advantages. In particular, the neuromorphic (or neuro-inspired) functionality provides smart capabilities to the system, by enabling the chip to learn from data in real-time. The neuromorphic architectures are also fast, yet energy efficient and have more compact ASIC implementations than traditional computing chips, especially if implemented with emerging device technologies like memristors [4]. Therefore, a distributed network of neuromorphic computing chips can provide integration into the densest possible system for the highest resolution and real-time performance.

Figure 2A:
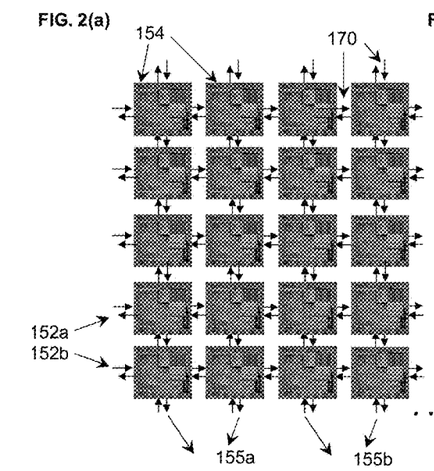
FIG. 2(a) shows the distributed network of neuromorphic computing chips with interconnections that enable the inputs and outputs signals to be shared between neighbors.

In the embodiment of FIG. 2(a), the neuromorphic computing chips (154) can be organized in an array, for example arranged in rows and columns implementing a cellular neural network maps for example. A cellular neural network maps well to a spatiotemporally distributed architecture. It is based on a fixed number of interconnected processing units called cells which map well to the sensor/computing/actuator processing units proposed (150). The cellular neural network topology combines the locality of the data processing in the computing unit (154) with the global diffusion of information thanks to the interconnectivity between neighboring units (170).

The embodiment shown in FIG. 1 shows how the distributed network from FIG. 2(a) can be mapped to the physical implementation. Only the computing chips (154) communicate with each other via the interconnections (170). Each unit (154) communicates with one or more immediately adjacent units (154). In the example shown in FIG. 1, each unit (154) can bi-directionally communicate with four neighboring units, two units in the same row and two units in the same column. More complex connectivity is possible for example diagonally across rows or columns, but it is not shown for clarity. The bi-directional interconnections (170) between computing chips (154) enable the sharing of the processed sensory inputs (152a) from the local chips to the neighboring chip and processed sensor data (152b) from the neighboring chip to the local chips. And similarly, the output signals (155a) from the local chips to the neighboring chips and the output signals (155b) from the neighboring chips to the local chips. This process, repeated for each chip in the entire network, leads to the indirect propagation of data at the global level, as the data from a chip is used by its neighbors in a scaled way to calculate their own outputs, which then are passed on to their own outputs to their respective neighbors, etc. Therefore, this distributed topology combines the locality of the data processing in the unit (150) with the global diffusion of information thanks to the interconnectivity between neighboring units (170). This enables the calculation of the data pattern across the entire network of sensors with distributed computing chips without having a central processing unit.

A sensor (152) sends its data only to its local chip (154) which pre-processes it and then distributes it to its neighboring chips (154) as pre-processed sensory data (152a). Neighboring chips sends this chip their own pre-processed sensory data (152b). A chip (154) shares its computation output to its neighboring chips (155a). Neighboring chips sends this chip their own computation output data (155b). However, the chip provides a control signal just to its local actuator (156) after its computation output was post-processed to the appropriate range of signals for the actuator. Other embodiments are possible as described below.

Figure 2B:
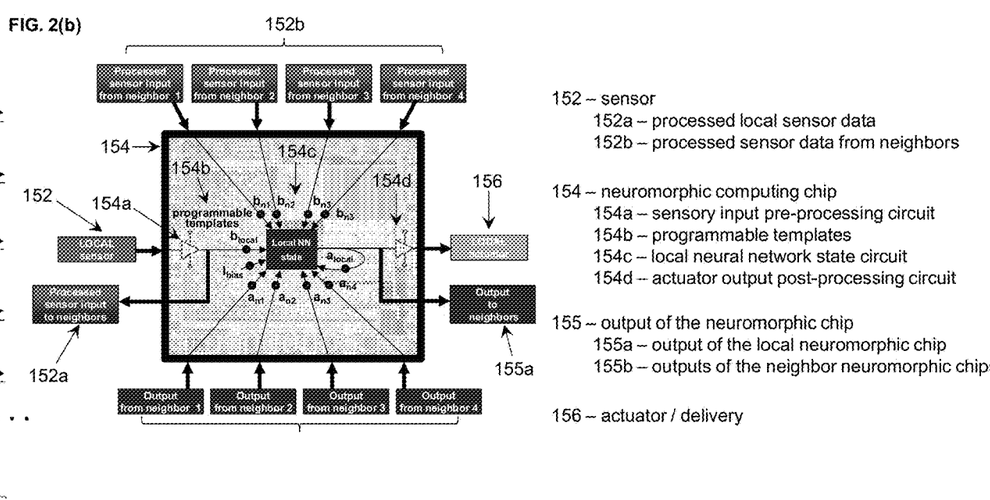
FIG. 2(b) shows a schematic of the functionality of a neuromorphic chip that has a core local neural network (NN) state circuit which determines the output to the actuator based on a set of programmable templates, the inputs from the local and neighboring sensors inputs and the outputs of the local and neighboring chips.

The embodiment of FIG. 2(b) shows one example of the functionality of a neuromorphic computing chip, but more implementations are possible depending on the complexity of the network and desired functionality. The chip has as inputs the data from its local sensor (152) which will process in real time via an on-chip sensory input pre-processing circuit (154a); the processed sensory data (152b) from neighboring chips; its own output data (155a) and the output data (155b) from neighboring chips. Each of this data gets scaled by its corresponding programmable value in the template matrices A and B (154b). This process is called weighting, where the data vectors get multiplied correspondingly with the templates. The data from each sensor is assigned a weight, based on its importance for the correct functionality of the network. For example, if the local sensor has a data value of 2 and its corresponding scale or weight value is 0.1, it is given a scaled value of 1 (2×0.5), and if the neighboring sensor has a data value of 3 and a corresponding scale or weight value of 0.1, it is given a scaled value of 0.3 (3×0.1). All the scaled data together with a bias value used for increased reliability of the computation serve as input to a local neural network state circuit (154c) which is the computing core of the chip. The local NN state circuit then generates one output value, which is fed back as input as needed.

Figure 2C:
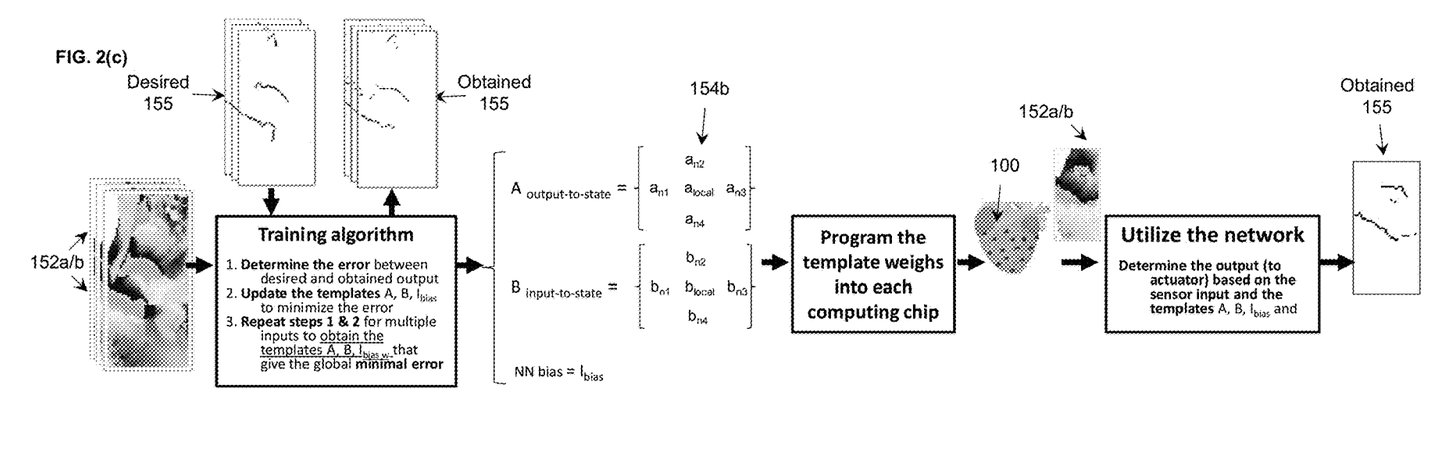
FIG. 2(c) is a schematic of a training algorithm.

In a cellular neural network, the state (154c) is calculated using the differential equation based on the scaled values of the inputs and outputs in the neighborhood and two matrices A and B which link the outputs and the inputs to the state respectively. The scaled values can be organized in matrices. These scale (weight) matrices are called templates and are used repeatedly for each processing unit. This calculation happens as part of the local NN state circuit. The optical values for these scale (weight) matrices are determined using a process called training. Training the network means determining the values of templates A and B based on desired outputs (FIG. 2(c)) using algorithms like backpropagation or random weight update, such as shown in reference [5] below, and it can be done externally via a computer, then programmed in the weight devices, or on-chip via dedicated circuit. Once the templates are set in the distributed network, the system can be deployed and used to extract the wavefront information from new inputs.

Given its local, highly parallel configuration, the cellular network has a simple implementation, fast calculation of the sensor data pattern and actuator activation. However, the cellular network approach could have limited predictive capacity since there is no global monitor. Accordingly, neural network topologies with a central processing unit can be provided for higher reliability, depending on the application. Other implementations of the local neural network state circuit (154c) can be envisioned based on other types of neural networks, such as feedforward or convolutional.

The output value is then post-processed by an actuator output post-processing circuit (154d) which converts it to the appropriate range of signals needed to actuate the delivery device (156).

There are various communications that can occur. In one embodiment, the chip (154) gets data from the sensor (152), pre-process it and then uses it for itself and distributes it to the neighbors. The chips (154) in this solution might be smaller. In another embodiment, the sensor (152) sends the data to its own chip (154) and the neighbor chips (154), and each chip does its own pre-processing. The chips might be larger since they need to pre-process circuits (154a) to handle data from multiple sensors, but the solution as a whole might be more noise robust since each chip operates on sensor data pre-processed locally on that chip. The chips also communicate to each other by sharing their outputs, e.g., outputs go to the actuation but also to their neighboring chips.

Thus, the chips 154 are implanted in the body. The sensors 152 can gather the data and the chips 154 can determine where the anomalous wavefront is located, then apply suitable energy pulses, such as a train of low energy pulses shown in [3], locally only in that area via the actuator 156. The sensed signal need not be sent to a centrally located processor for analysis. And, a localized pulse can be applied by the actuator 156, rather than applying a very large purse to the whole organ (e.g., heart). The small controlled local pulses applied via the actuator 156 are possible because the processors 154 are implanted and process the sensor data in high definition.

Alternative ways of computing and interconnection can also be provided. For example, the sensors (152) can send the data directly to the local chip (154) and to the neighbor chips, and each chip does the preprocessing. The smart distributed network 100 can be positioned about an organ such as a heart, such as by being incorporated in a sleeve that can be positioned about the organ. However, embodiments for other electro-active organs based on a similar principle can be provided, such as smart patches for the brain, muscle or gut.

Figure 3A:
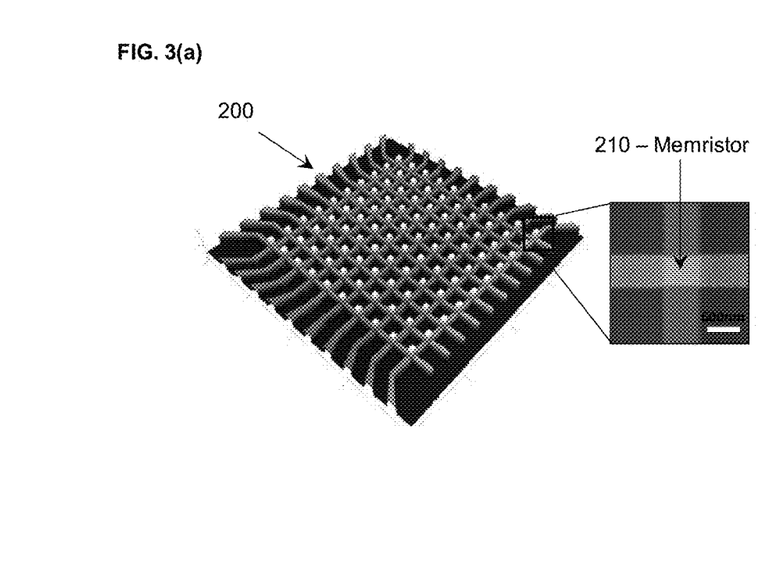
FIG. 3(a) matrix of programmable memristors and memristor device and FIG. 3(b) is a memristor programmed to 16 conductance values, which are stored stably in time.

The programmable templates (154b) can be manufactured using emerging devices, such as resistive switching matrices of devices (200) called memristor or RRAM (210), shown in FIG. 3(a). Each weight in the template, such as $a_{local}$, $a_{n1}$ . . . $a_{n4}$, can have its value stored physically as a conductance in a memristor. The advantage is that metal-oxide memristors (210) are compact memory devices which can be manufactured <10 nm in dimensions, so thousands of memristors could fit in a 50 μm neuromorphic computing chip thus increasing its computational functionality if needed. A memristor can be programmed as desired to many conductance states (220) between an ON value of high conductance (220a) and an OFF value of low conductance (220b) [4] and can be used for neuromorphic computing, for example as shown in reference [6]. Memristors are non-volatile—they retain their programmed conductance value in time without extra energy consumption. Their small size, programmability and non-volatility makes them suitable for embedded applications where compactness is crucial and energy is scarce such as biomedical applications.

Figure 4:
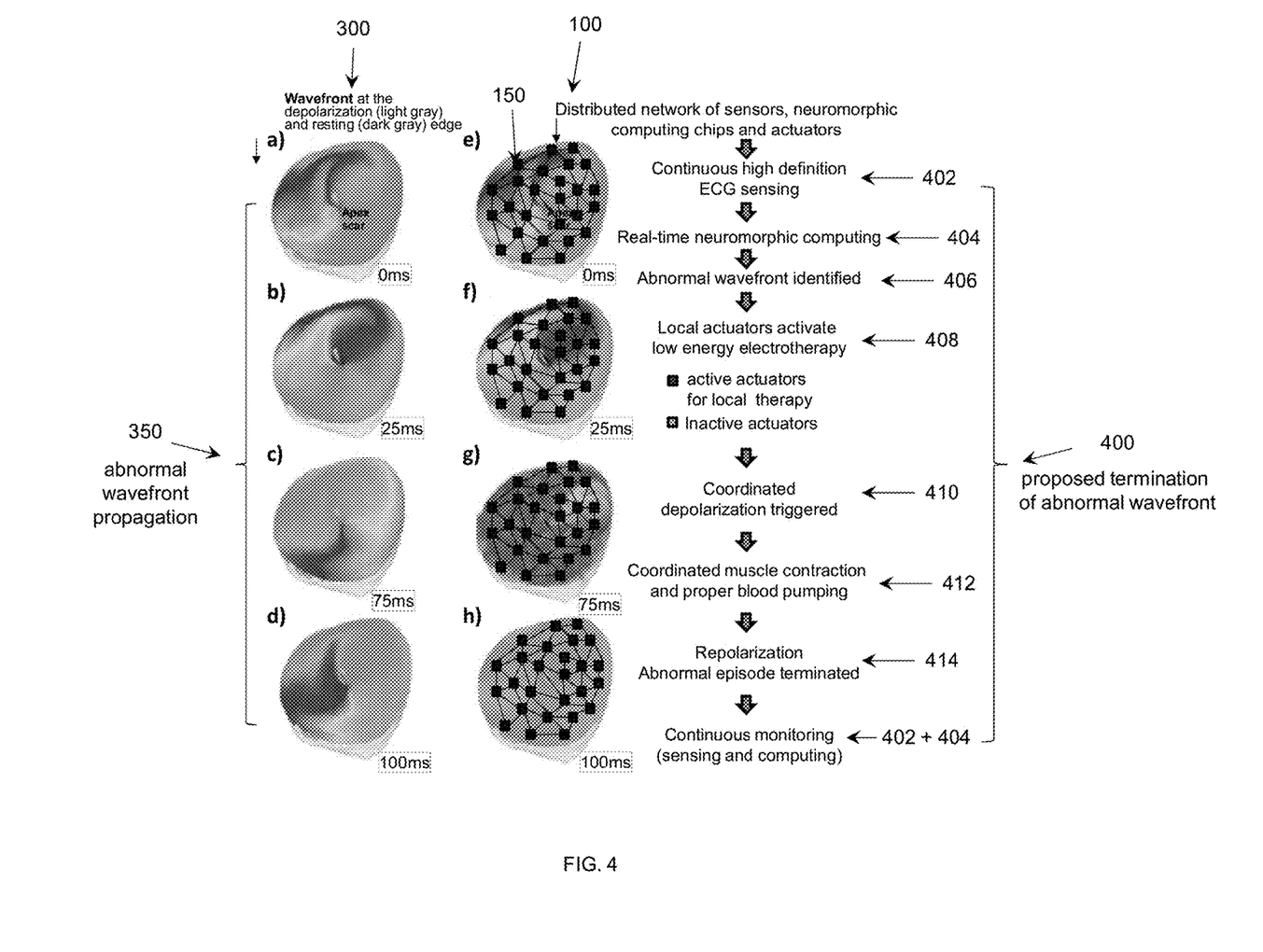
FIG. 4 shows ventricular tachycardia activation wavefront and its proposed local termination: a) Example of abnormal cardiac wave propagation maps showing the wavefront propagating as a rotor around the apex of the heart (data obtained using optical imaging of a rabbit heart), and b) a corresponding solution for local real-time termination of tachycardia or fibrillation using the proposed distributed network of sensors, neuromorphic computing chips and actuators.

Turning to FIG. 4, the functionality of the system for abnormal wavefront detection and termination (400) is described. FIG. 4(a) exemplifies abnormal cardiac wave propagation maps showing the wavefront propagating in a very fast rotor around the apex of the ventricle. The data obtained using optical imaging shows different activation of the tissue characteristic of an abnormal wavefront (the edge between black and light gray). The wavefront is propagating like a fast electrical storm with conduction velocity of 10-100 cm/sec (FIGS. 4(a)-(d)). In normal propagation, the entire tissue is activated (black) or relaxed (light gray) with similar velocities (FIGS. 4(g), 4(h)). When the tissue is activated (black), the muscle contracts. The entire ventricle needs to contract synchronously for the blood to be pumped properly. In abnormal wavefront propagation, only a small portion of the tissue is activated at a time in an erratic pattern, thus preventing the ventricle to properly contract.

FIG. 4(b) shows an example of how the distributed network of sensors, neuromorphic computing chips and actuators (100) can be used for the local analysis of the bioelectric data in real time and with high spatial definition. The distributed network consists of a high number of processing units (150) thus enabling high spatial resolution. Each processing unit has to operate very fast on the same timescale with the electrical activity in the organ, for example on the order of milliseconds for the heart, thus enabling real time processing. In one embodiment, the actuator applies an output pulse or sequence of pulses within 10-100 ms from when the sensor detects the sensed signal, which includes the time for the processing unit to receive the sensed signal, analyze the signal and provide a control signal to the actuator. In another embodiment, the real time operation can be preferably ~1 ms. That real time processing is achieved by the sensor and actuator being connected to the processing chip and the processing chip being located at the organ. And the system is distributed in that it has hundreds of sensors and a separate computing chip for each sensor to process data from that sensor. Since the data from the sensor is processed locally, sensor data can be processed faster by a small chip. And by having a network of processing units, the system can provide reliable and local therapeutic pulses.

The distributed network performs continuous sensing (402) across the entire region via its high number of integrated sensors (152). The data from the sensors is analyzed continuously and in real-time (404) by the integrated neuromorphic computing chips (154). If an abnormal wavefront is identified (406), the network reacts fast to actuate only the delivery devices in the region of excitable gap ahead of the wavefront (408) to deliver local electrotherapy pulses which are lower energy than a defibrillation shock on the entire heart as currently in use. These local electrotherapy pulses trigger a tissue response that promotes a coordinated activation (depolarization) of the entire ventricle (410). The activation of the entire ventricle leads to a coordinated muscle contraction and thus proper blood pumping in the heart (412). After the coordinated activation, the muscle can relax (repolarize) in a coordinated fashion as well, thus the abnormal episode is terminated (414). The monitoring of the heart electrical activity continues via sensing and computing (416) to prevent in a similar fashion future abnormal arrhythmic episodes.

Figure 5:
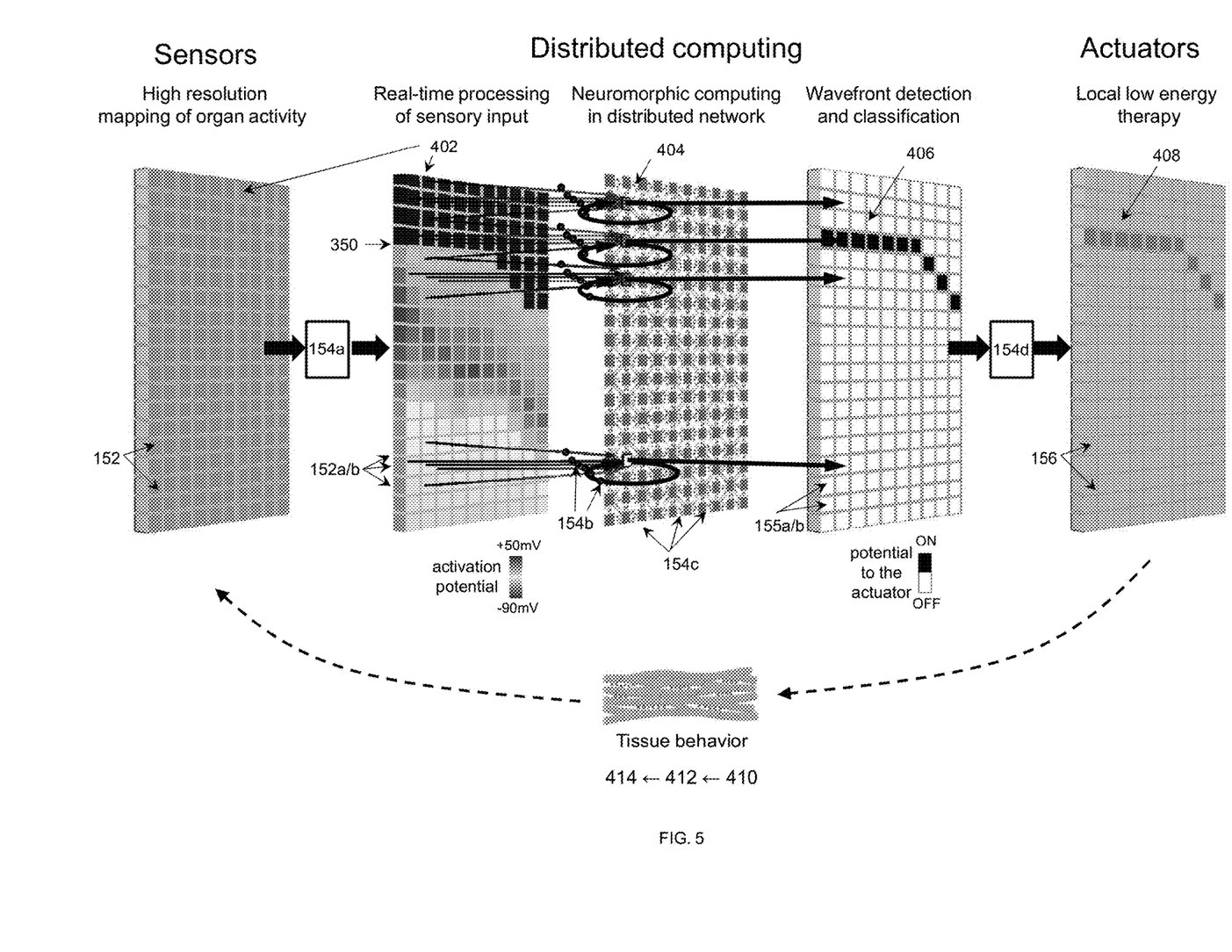
FIG. 5 is a schematic of distributed computing that allows for high definition mapping, interpretation and response for wavefront detection and termination. The sensory input is pre-processed in real time by on-chip circuit blocks. They are scaled according to the programmable templates, then processed by the core local neural network (NN) state circuit blocks. The outputs of each neuromorphic computing are scaled according to their corresponding programmable templates and fed back to the network for real-time processing and actuation. At each time step, the outputs are also post-processed and converted into desired signal to activate the actuators and provide low energy electrotherapy only at the edge of the abnormal wavefront (black).

FIG. 5 shows an example of how distributed computing allows for high definition mapping, interpretation and response for wavefront detection and termination. The sensory input is recorded by the sensors (152) then pre-processed in real time by circuit blocks (154a) on the computing chip (154). This is the continuous high definition sensing of the organ activity (402). These pre-processed inputs (152a, b) are scaled according to the programmable templates (154b), then processed by the core local neural network (NN) state circuit blocks. The outputs of each neuromorphic computing are scaled according to their corresponding programmable templates and fed back to the network (i.e., its neighbors) for real-time processing. At each time step, the outputs are also post-processed and converted into desired signal to activate the actuators and provide ultra-low energy electrotherapy only at the edge of the abnormal wavefront (black) (408). Additional chips with wireless capability can be incorporated in the network so the physician can use external/remote monitor to check and control the system as to the status, patient condition, etc.

The actuator 156 would then apply a small pulse to depolarize the nearby normal tissue and trigger a synchronized depolarization of the entire muscle syncytium, stopping the fibrillation and restoring the normal beat. The pulses can be applied only by a selected subset of actuators, for example only those actuators that are near the detected anomaly within an excitable gap ahead of propagating arrhythmic wavefront, and can either be equal in magnitude or different depending on the distance from the anomaly and/or the type of anomaly. The pulses can vary in magnitude and shape and can be applied either simultaneously or at different periods of time depending on the sensed patient condition and application.

Figure 6:
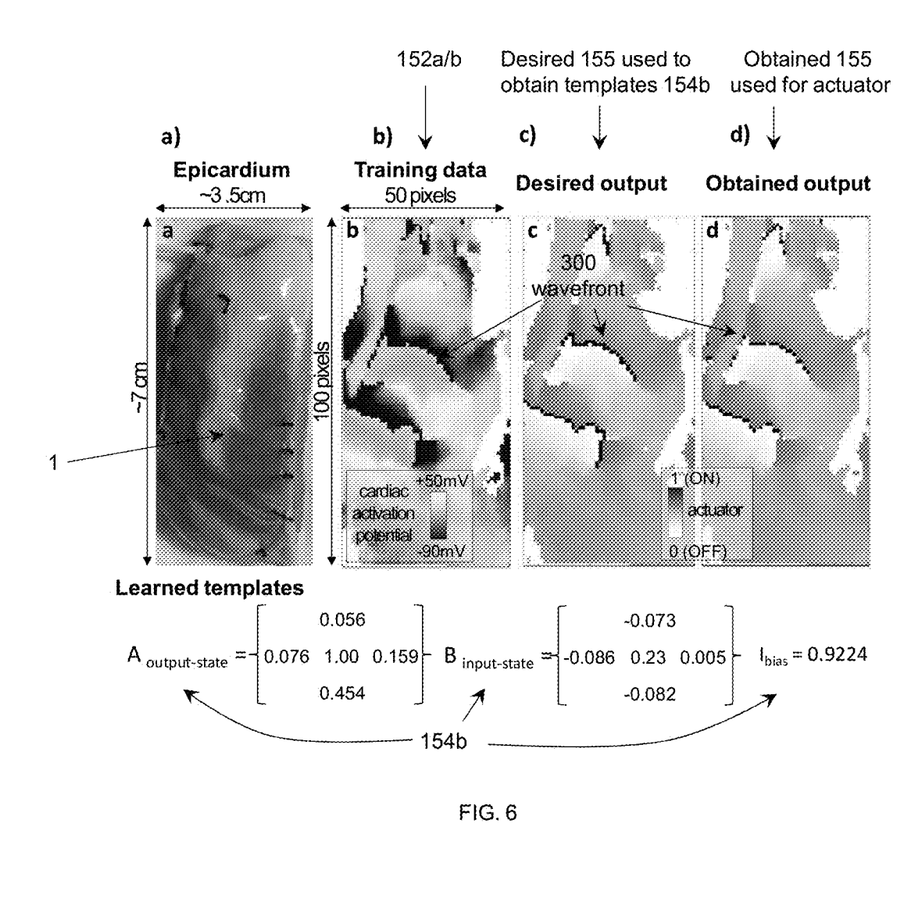
FIG. 6 shows results of cellular neural network algorithm for wavefront detection (a) human epicardium ventricular tissue; (b) recorded data; (c) standard method (wavefronts are isophase lines along $\phi(t)=\pi$) and (d) wave front detection with cellular neural network mappable to memristors.

FIG. 6 shows results of a cellular neural network algorithm to detect wave fronts in optically recorded cardiac data. Optically recorded data were used due to the high resolution. However, these results are directly applicable to electrically recorded data. The optical data were captured from a left ventricle wedge preparation with a high-resolution camera. The resolution is 100×50 pixels.

In one embodiment in FIG. 6(b), 100×50 cellular neural processing units 154 were used, with each unit connected to nine sensors 152 to receive sensory inputs—from local and closest neighbors. Each unit 154 has one binary output. A binary batch backpropagation training algorithm suitable for this application where the output obtained after each epoch is binarized before calculating the loss to update the weights. This training algorithm shows better results that the ones reported in literature [5]. When the templates obtained during training are used on cardiac data maps, it shows good estimations of the wavefronts (obtained 155) (FIG. 6(d)) by comparison with the desired estimation (desired 155) (FIG. 6(c)). The peak performance is achieved around batch size equals 7, leading to a 99.64% accuracy, 91.2% precision, 96.85% sensitivity, 99.72% specificity. This algorithm is directly mappable to hardware as explained above and shown in FIG. 2. This algorithm is possible because of the local computing chips co-located with the sensors.

Figure 3B:
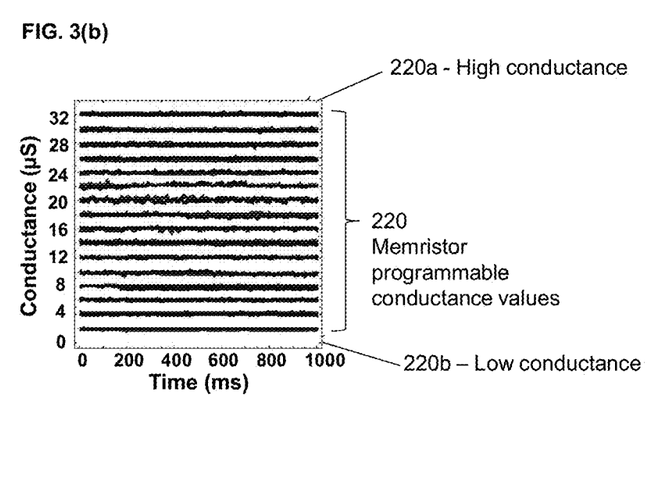

This algorithm can be translated into a network of hardware chips using hybrid memristor for weight storage and transistor devices for programming, FIGS. 2 and 3. The template weights will be determined via the software algorithm then imported on the chip (154) via sequential programming of each memristor (220). Estimates of distributed computing [7] have an area of a processing unit of ~10×10 μm² in 45 nm node chips and a detection speed of 50 ns, showing promise of our real-time compact computing approach.

The invention enables the development of a transformative distributed hardware for the integrated gathering and computing of high definition biomedical data. This approach can revolutionize the next-generation implantable biomedical technologies. It opens the path to computing of multiphysics data in the heart and in other organs as required for the reliable diagnostics and therapy for a wide variety of pathological conditions.

The following references are hereby incorporated by reference.

[1] L. Xu et al., "3D multifunctional integumentary membranes for spatiotemporal cardiac measurements and stimulation across the entire epicardium," *Nature Communications,* vol. 5, p. 3329, 2014.

[2] S. R. Gutbrod, M. S. Sulkin, J. A. Rogers, I. R. Efimov, "Patient-specific flexible and stretchable devices for cardiac diagnostics and therapy," *Progress in biophysics and molecular biology,* vol. 115, no. 2-3, pp. 244-251, 2014.

[3] A. H. Janardhan et al., "A Novel Low-Energy Electrotherapy That Terminates Ventricular Tachycardia With Lower Energy Than a Biphasic Shock When Antitachycardia Pacing Fails," *Journal of the American College of Cardiology,* vol. 60, no. 23, pp. 2393-2398, December 2012.

[4] G. C. Adam, B. D. Hoskins, M. Prezioso, F. Merrikh-Bayat, B. Chakrabarti, and D. B. Strukov, "3-D Memristor Crossbars for Analog and Neuromorphic Computing Applications," *IEEE Transactions on Electron Devices,* vol. 64, no. 1, pp. 312-318, 2017.

[5] S. P. Adhikari, H. Kim, C. Yang, and L. O. Chua, "Building cellular neural network templates with a hardware friendly learning algorithm," *Neurocomputing,* vol. 312, pp. 276-284, 2018.

[6] M. Prezioso, F. Merrikh-Bayat, B. D. Hoskins, G. C. Adam, K. K. Likharev, B. D. Strukov "Training and operation of an integrated neuromorphic network based on metal-oxide memristors" *Nature,* vol. 521, no. 7750, 61, 2015.

[7] W. Zhang and N.-J. Wu, "CMOL-based cellular neural networks and parallel processor for future image processing," in *Proceedings of the 8th IEEE Conference on Nanotechnology,* pp. 737-740, 2008.

The foregoing description and drawings should be considered as illustrative only of the principles of the invention. The invention may be configured in a variety of shapes and sizes and is not intended to be limited by the embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A medical apparatus for an organ or a tissue, comprising:
    a flexible or stretchable patch or a sleeve that conforms to a shape of the organ or a tissue, said flexible or stretchable patch or sleeve having a rigid substrate; and
    a plurality of computing processing units directly coupled to or embedded in said substrate and distributed throughout said substrate, each of said plurality of processing units having a sensor for sensing a condition of the organ or tissue and providing a sensed signal; each of said plurality of computing processing units including a computing device that receives the sensed electrical signal from said sensor, analyzes the sensed signal, and provides a control signal; and each of said computing processing units further including an actuator for applying an output stimulus to the tissue in response to the control signal from said computing device,
    wherein said apparatus comprises an implantable device.

2. The apparatus of claim 1, wherein said sensor and said actuator are directly connected to said computing device.

3. The apparatus of claim 1, wherein said substrate conforms to a shape of the organ or tissue.

4. The apparatus of claim 1, wherein said plurality of computing processing units are non-intrusive in size to the tissue.

5. The apparatus of claim 1, wherein said computing device receives information from an adjacent two or more of said plurality of computing processing units.

6. The apparatus of claim 1, wherein said computing device sends information to adjacent two or more of said plurality of computing processing units.

7. The apparatus of claim 1, wherein said output comprises of a therapeutic stimulus or a therapeutic sequence of stimuli.

8. The apparatus of claim 1, wherein said plurality of computing processing units are embedded in said substrate.

9. The apparatus of claim 1, wherein said sensor, said computing device and said actuator form a closed loop of data processing.

10. The apparatus of claim 1, further comprising interconnections connecting said plurality of computing processing units, and/or connecting the computing device of neighboring ones of said plurality of computing processing units.

11. The apparatus of claim 1, wherein said computing device receives the sensed signal, analyzes the sensed signal, and provides the control signal in real time.

12. The apparatus of claim 1, wherein said actuator applies the output stimulus in real time with respect to the sensor providing the sensed signal.

13. The apparatus of claim 1, wherein said plurality of computing processing units for a distributed network of said plurality of computing processing units.

14. The apparatus of claim 1, said computing device extracting diagnostic-relevant features to determine the control signal.

15. The apparatus of claim 14, said computing device physically implements machine learning or neuromorphic computing algorithms.

16. The apparatus of claim 1, wherein said computing device sends information to adjacent two or more of said plurality of computing processing units.

17. The apparatus of claim 1, wherein said plurality of computing processing units operate in real-time.

18. The apparatus of claim 1, further comprising interconnections connecting the computing device of neighboring ones of said plurality of computing processing units.

19. A medical apparatus for tissue, comprising:
    a substrate that is a flexible or stretchable patch or a sleeve that conforms to a shape of the tissue; and
    a plurality of computing processing units connected to said substrate and distributed throughout said substrate, each of said plurality of processing units having a sensor for sensing a condition of the tissue and providing a sensed signal; each of said plurality of computing processing units including a computing processing device that receives the sensed electrical signal from said sensor, analyzes the sensed signal and provides a control signal; and each of said computing processing units further including an actuator for applying an output stimulus to the tissue in response to the control signal from said computing device, wherein said computing device comprises a neuromorphic chip or machine learning chip.

20. The apparatus of claim 19, said computing device extracting diagnostic-relevant features to determine the control signal.

21. The apparatus of claim 20, said computing device physically implements machine learning or neuromorphic computing algorithms.

22. The apparatus of claim 19, wherein said substrate is flexible or conforms to a shape of the tissue.

23. The apparatus of claim 19, wherein said computing device receives information from an adjacent two or more of said plurality of computing units.

24. The apparatus of claim 19, wherein said output comprises of a stimulus or a sequence of stimuli.

25. The apparatus of claim 24, wherein said output stimulus or sequence of stimuli comprise a therapeutic stimulus or a therapeutic sequence of stimuli.

26. The apparatus of claim 19, wherein said plurality of computing processing units are embedded in said substrate.

* * * * *